United States Patent [19]

Brombacher et al.

[11] Patent Number: 4,544,659
[45] Date of Patent: Oct. 1, 1985

[54] SCHISTOSOMICIDAL ACRIDANONE HYDRAZONES

[75] Inventors: Urs Brombacher, Riehen; Marc Montavon, Basel, both of Switzerland; Hermann Bretschneider; Joachim Schantl, both of Innsbruck, Austria; Wolfgang Türk, Ludwigshafen am Rhein, Fed. Rep. of Germany

[73] Assignee: Hoffman-La Roche Inc., Nutley, N.J.

[21] Appl. No.: 551,816

[22] Filed: Nov. 15, 1983

[30] Foreign Application Priority Data

Nov. 26, 1982 [CH] Switzerland .................. 6895/82

[51] Int. Cl.$^4$ .................. A61K 31/47; C07D 219/08
[52] U.S. Cl. .................. 514/297; 546/106
[58] Field of Search .................. 546/106, 105; 424/257

[56] References Cited

U.S. PATENT DOCUMENTS

| 3,712,943 | 1/1973 | Mayer et al. | 424/257 X |
| 3,936,444 | 2/1976 | Botta | 546/162 |

FOREIGN PATENT DOCUMENTS

| 0094982 | 10/1922 | Switzerland | 546/105 |
| 0096608 | 11/1922 | Switzerland | 546/105 |
| 1068595 | 5/1967 | United Kingdom . | |

OTHER PUBLICATIONS

Hünig, et al., Chemical Abstracts, vol. 55, 12857h–12859f (1961).
Zhang, et al., Chemical Abstracts, vol. 93, 239185w (1980).
Ioffe, et al., Chemical Abstracts, vol. 71, 61177a and 70475y (1969).
Elslager, et al., Chemical Abstracts, vol. 72, 3335k (1970).

*Primary Examiner*—Donald G. Daus
*Assistant Examiner*—Diana G. Rivers
*Attorney, Agent, or Firm*—Jon S. Saxe; Bernard S. Leon; Matthew Boxer

[57] ABSTRACT

Acridanone derivatives of the formula

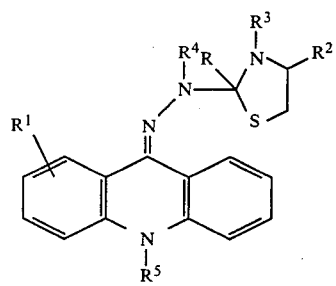

wherein the dotted line is an optional bond, $R^1$ is hydrogen, halogen or nitro, $R^2$ is hydrogen or lower alkyl, one of the substituents $R^3$ and $R^4$ is hydrogen or lower alkyl and the other together with R is an additional bond and $R^5$ is hydrogen, lower alkyl, lower alkenyl, lower alkynyl or lower alkyl substituted by halogen or lower alkoxy, and pharmaceutically acceptable acid addition salts thereof, processes for their preparation and pharmaceutical compositions based thereon, are described. The compounds of formula I are useful as schistosomicidal agents.

18 Claims, No Drawings

SCHISTOSOMICIDAL ACRIDANONE HYDRAZONES

BRIEF SUMMARY OF THE INVENTION

The invention relates to acridanone derivatives of the formula

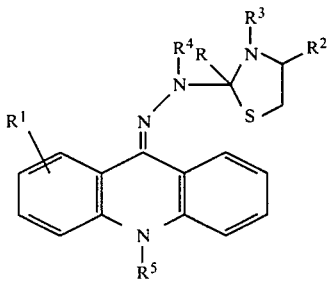

wherein the dotted line is an optional bond, $R^1$ is hydrogen, halogen or nitro, $R^2$ is hydrogen or lower alkyl, one of the substituents $R^3$ and $R^4$ is hydrogen or lower alkyl and the other together with R is an additional bond and $R^5$ is hydrogen, lower alkyl, lower alkenyl, lower alkynyl or lower alkyl substituted by halogen or lower alkoxy
and pharmaceutically acceptable acid addition salts thereof.

The compounds possess valuable pharmacological properties and can be used in the control or prevention of schistosomiasis.

DETAILED DESCRIPTION OF THE INVENTION

The invention relates to acridanone derivatives of the formula

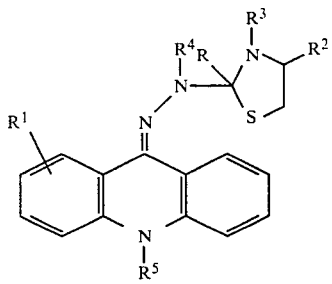

wherein the dotted line is an optional bond, $R^1$ is hydrogen, halogen or nitro, $R^2$ is hydrogen or lower alkyl, one of the substituents $R^3$ and $R^4$ is hydrogen or lower alkyl and the other together with R is an additional bond and $R^5$ is hydrogen, lower alkyl, lower alkenyl, lower alkynyl or lower alkyl substituted by halogen or lower alkoxy,
and pharmaceutically acceptable acid addition salts thereof.

The compounds possess valuable pharmacological properties and can be used in the control or prevention of schistosomiasis.

Objects of the invention are acridanone derivatives of formula I and their pharmaceutically acceptable salts, the preparation of these compounds and salts, intermediates for their preparation, medicaments containing the compounds of formula I and salts and the preparation of such medicaments.

The term "lower" as used in the present description signifies that the compounds or groups denoted in such a manner contain up to 4 carbon atoms and can be straight-chain or branched-chain. The term "lower alkyl" denotes saturated hydrocarbon groups such as methyl, ethyl, n-butyl and the like. The term "lower alkenyl" denotes hydrocarbon groups which contain an olefinic double bond such as allyl and the like. The term "lower alkynyl" denotes hydrocarbon groups which contain a triple bond such as propargyl and the like. The term "lower alkoxy" denotes lower alkyl groups linked via an oxygen atom such as methoxy and the like. The term "lower alkyl substituted by halogen or lower alkoxy" includes groups such as 2-chloroethyl, 2,2-methoxyethyl, 2,2-dimethoxyethyl and the like. The term "halogen" denotes fluorine, chlorine, bromine or iodine.

Depending on the significance of the dotted line and of the substituents R, $R^3$, $R^4$ and $R^5$, the compounds of formula I above can be present in various tautomeric forms. The invention includes all possible tautomeric forms.

In formula I, $R^1$ preferably is hydrogen. $R^2$ preferably is hydrogen. Preferably, one of the substituents $R^3$ and $R^4$ is hydrogen and the other together with R is an additional bond. $R^5$ preferably is hydrogen or lower alkyl.

A particularly preferred compound provided by the invention is 10-methyl-9-acridanone (2-thiazolyl)hydrazone.

Other preferred compounds of formula I are 9-acridanone (2-thiazolidinylidene)hydrazone, 9-acridanone (2-thiazolyl)hydrazone, 10-methyl-9-acridanone (2-thiazolidinylidene)hydrazone, 10-ethyl-9-acridanone (2-thiazolidinylidene)hydrazone, 9-acridanone methyl (2-thiazolinyl)hydrazone and 10-(2-methoxyethyl)-9-acridanone (2-thiazolidinylidene)hydrazone.

The acridanone derivatives of formula I and their pharmaceutically acceptable acid addition salts can be prepared in accordance with the invention as follows:

(a) cyclizing a compound of the formulas

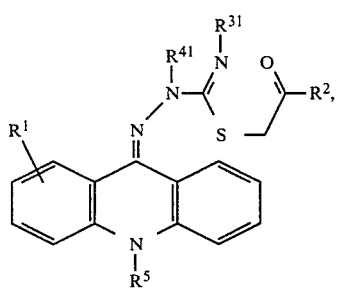

II

-continued

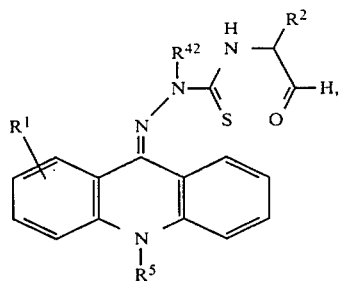

III

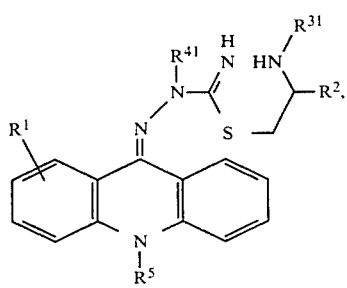

IV

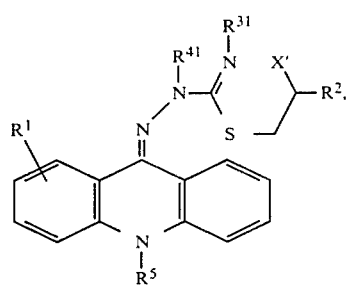

V

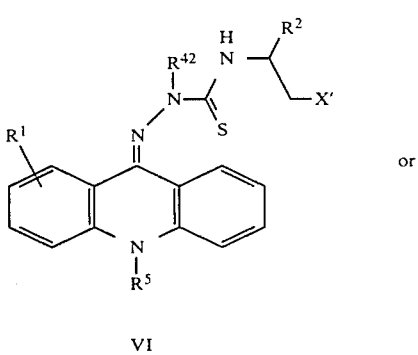

VI

-continued

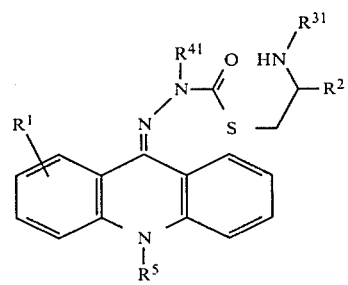

VII wherein one of $R^{31}$ and $R^{41}$ is hydrogen or lower alkyl and the other is hydrogen, $R^{42}$ is hydrogen or lower alkyl, X' is a leaving group and $R^1$, $R^2$ and $R^5$ are as previously described, or (b) reacting a compound of the formula

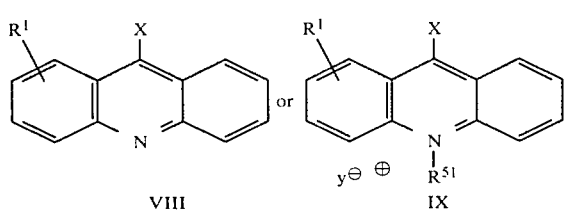

VIII    IX wherein $R^{51}$ is lower alkyl, lower alkenyl, lower alkynyl or lower alkyl substituted by halogen or lower alkoxy, X is a leaving group, $Y^\ominus$ is an anion and $R^1$ is as previously described.

with a compound of the formula

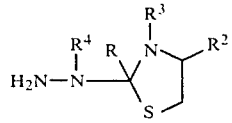   X wherein the dotted line, R, $R^2$, $R^3$ and $R^4$ are as previously described, or (c) reacting a compound of the formula

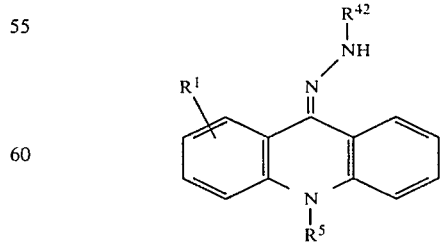   XI wherein $R^{42}$ is hydrogen or lower alkyl and $R^1$ and $R^5$ are as previously described, with a compound of the formula

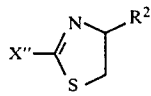

wherein X" is a leaving group and $R^2$ and the dotted line are as previously described,
and (d) if desired, converting a compound of formula I obtained into a pharmaceutically acceptable acid addition salt.

In accordance with process variant (a), the compounds of formula I can be prepared by cyclizing a compound of formula II, III, IV, V, VI or VII according to methods which are known and which are familiar to any person skilled in the art. The leaving group denoted by X' in formulas V and VI is preferably a halogen atom, especially bromine or chlorine. Depending on the starting material used, the ring closure reaction is carried out fairly readily and can be accomplished or completed, if necessary, by standing for a long time and/or by applying heat. The starting materials for the ring closure reaction need not necessarily be used in isolated form. As a rule, it has been found to be convenient to cyclize these starting materials directly or to leave these starting materials to cyclize without isolation from the reaction mixture in which they have been prepared. Depending on the reaction conditions used, in some cases an isolation is even not possible, since the cyclization takes place spontaneously.

Suitable solvents for the process variant (a) are, for example, ethers such as tetrahydrofuran, dioxane, ethylene glycol dimethyl ether, diethylene glycol dimethyl ether and the like, alcohols such as methanol, ethanol and the like, dimethylformamide, dimethyl sulfoxide, acetonitrile and the like. The reaction is conveniently carried out at a temperature in the range of about room temperature to the boiling point of the reaction mixture.

In accordance with process variant (b), the compounds of formula I can be prepared by reacting a compound of formula VIII or IX with a compound of formula X. The leaving group denoted by X in the compounds of formulas VIII and IX is preferably halogen, a lower alkanoyloxy group or a lower alkoxy group, especially chlorine, acetoxy or methoxy. While the compounds of formula VIII are as a rule stable substances, this is not always the case with the compounds of formula IX. The compounds of formula IX are therefore conveniently prepared shortly before the reaction with a compound of formula X from a compound of the formula

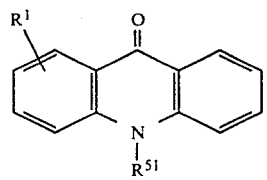

wherein $R^1$ and $R^{51}$ are as previously described, as set forth below and, optionally without previous isolation, processed directly.

The compound of formula X is conveniently used in the form of an acid addition salt, for example, in the form of a hydrochloride or hydrobromide. The reaction can be carried out in the presence of an acid-binding agent, especially suitable acid-binding agents are sodium and potassium carbonates, bicarbonates and acetates. Suitable solvents for process variant (b) are, for example, lower alcohols such as methanol and ethanol and other organic solvent which are inert under the reaction conditions such as dimethylformamide, acetonitrile and the like. The reaction is conveniently carried out at a temperature in the range of about room temperature to the boiling point of the reaction mixture.

In accordance with process variant (c), the compounds of formula I can be prepared by reacting a compound of formula XI with a compound of formula XII. The leaving group denoted by X" in formula XII is preferably halogen, for example, chlorine or bromine or the thiol group. The following organic solvents, which are inert under the reaction conditions, can be used: ethers such as tetrahydrofuran, dioxane, diethyl ether and the like, alcohols such as methanol, ethanol and the like, dimethylformamide, dimethyl sulfoxide, acetonitrile and the like. The reaction is conveniently carried out at a temperature in the range of about room temperature to the boiling point of the reaction mixture.

In accordance with process variant (d), the acridanone derivatives of formula I above can be converted into pharmaceutically acceptable acid addition salts. The preparation of such acid addition salts is carried out according to known methods. There come into consideration not only salts with pharmaceutically acceptable inorganic acids but also salts with pharmaceutically acceptable organic acids; for example, hydrochlorides, hydrobromides, sulfates, citrates, acetates, succinates, methanesulfonates, p-toluenesulfonates and the like.

The compounds of formulas II, III, IV, V, VI, VII and XI in which $R^5$ is hydrogen, used as starting materials, can be prepared from compounds of formula VIII, in accordance with Reaction Scheme I hereinafter, wherein $R^1$, $R^2$, $R^{31}$, $R^{41}$, $R^{42}$, X and X' are as previously described. $R^6$ and $R^7$ each is lower alkyl or together are lower alkylene and $R^8$ is lower alkyl, phenyl or substituted phenyl. The compounds of formula VIII used as starting materials are known or can be prepared in analogy to the known members of this class of substances.

Reaction Scheme I
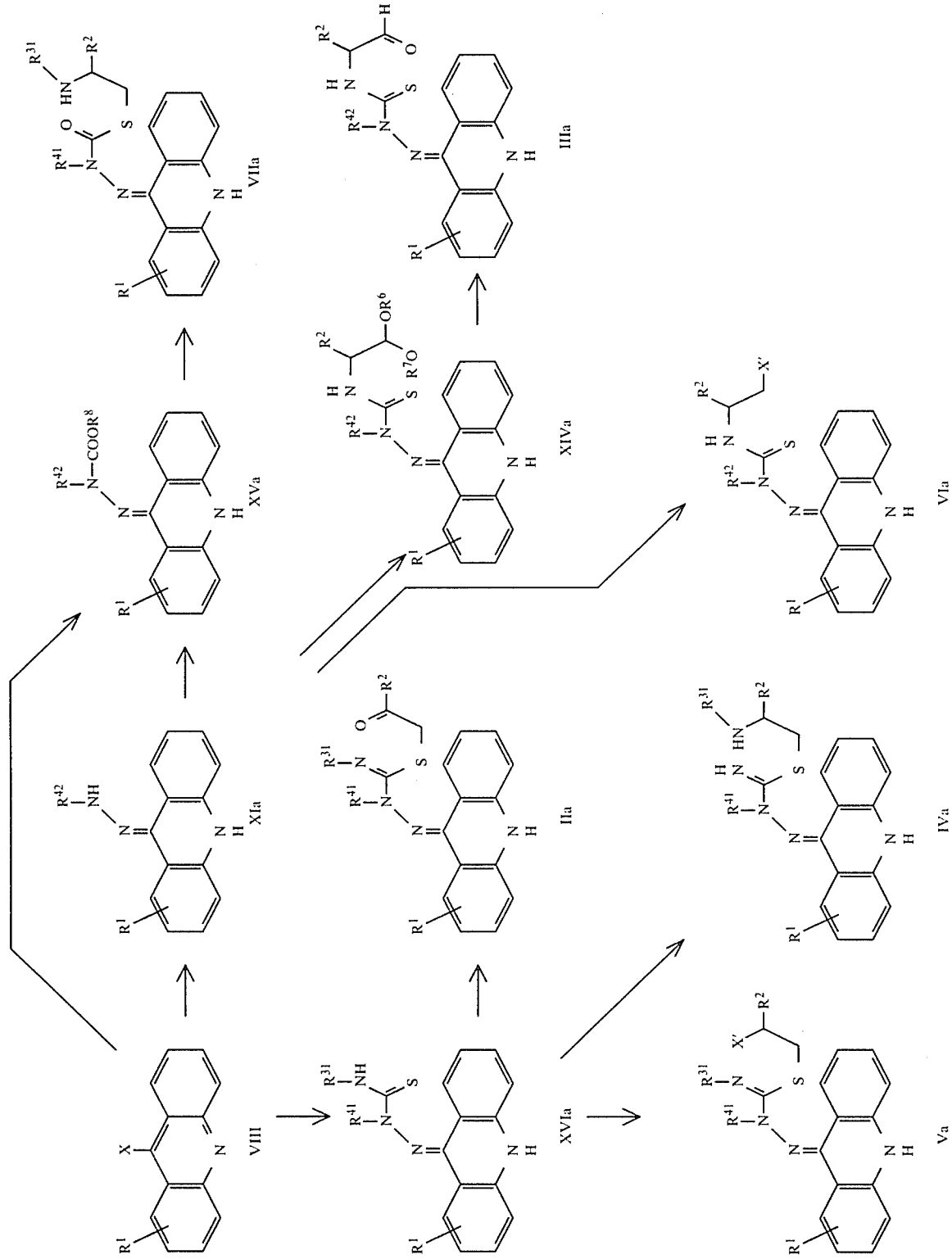

In Reaction Scheme I, the compounds of formulas XIa and XVIa can be prepared by reacting a compound of formula VIII with a hydrazine of the formula $H_2N-NH-R^{42}$ in which $R^{42}$ is as previously described or with a thiosemicarbazide of the formula $H_2N-NR^{41}-CS-NHR^{31}$ in which $R^{31}$ and $R^{41}$ are as previously described. These reactions can be carried out under the reaction conditions described above for process variant (b).

By reacting a compound of formula XVIa with a compound of the formula $X'-CH_2COR^2$ in which $X'$ and $R^2$ are as previously described there is obtained a compound of formula IIa. The leaving group denoted by $X'$ is preferably chlorine or bromine. Lower alcohols such as methanol and ethanol are especially suitable solvents. The reaction is conveniently carried out at a temperature in the range of about room temperature to the boiling point of the reaction mixture.

Compounds of formula IVa can be obtained by reacting a compound of formula XVIa in which $R^{31}$ is hydrogen with a compound of the formula $X'-CH_2-CHR^2-NHR^{32}$ in which $X'$ and $R^2$ are as previously described and $R^{32}$ is hydrogen or, where $R^{41}$ in the compound of formula XVIa is hydrogen, also lower alkyl. The amine is conveniently used in the form of an acid addition salt, the hydrochlorides or hydrobromides are preferred. Suitable solvents are, for example, lower alcohols such as methanol and ethanol, ethers such as tetrahydrofuran, dioxane and ethylene glycol dimethyl ether, dimethylformamide, dimethyl sulfoxide, acetonitrile and the like. The reaction is preferably carried out at a temperature between about room temperature and the boiling point of the reaction mixture.

Compounds of formula Va can be obtained by reacting a compound of formula XVIa in an inert organic solvent and at a temperature in the range of about room temperature to the boiling point of the reaction mixture with a compound of the formula $X'-CH_2-CHR^2-X'$ in which $X'$ and $R^2$ are as previously described, preferably a dichloride or dibromide is utilized. Suitable solvents are, for example, alcohols such as methanol, ethanol and the like, ethers such as tetrahydrofuran, dioxane and the like, dimethylformamide, dimethyl sulfoxide and the like.

The compounds of formula IIIa can be prepared by reacting a compound of formula XIa with an isothiocyanate of the formula

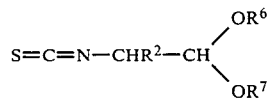

in which $R^2$, $R^6$ and $R^7$ are as previously described and subsequently hydrolyzing the acetal group in the resulting compound of formula XIVa. The first step is conveniently carried out in an inert organic solvent, for example, in an ether such as diethyl ether, t-butyl methyl ether and tetrahydrofuran or in dimethylformamide, acetonitrile of the like. at a temperature between about room temperature and the boiling point of the reaction mixture. The hydrolysis of the acetal group can be carried out by means of an aqueous acid, optionally in the presence of a solubilizer such as tetrahydrofuran, dioxane, methanol, ethanol, dimethylformamide or the like. The acid can be, for example, sulfuric acid, hydrochloric acid, p-toluenesulfonic acid and the like. The temperature is not critical and can vary in a wide range.

The compounds of formula VIa can be prepared by reacting a compound of formula XIa with an isothiocyanate of the formula $S=C=N-CHR^2-CH_2-X'$ in which $X'$ and $R^2$ are as previously described. This reaction can be carried out, for example, under the reaction conditions described above for the preparation of compounds of formula XIVa from compounds of formula XIa.

The compounds of formula VIIa can be prepared by treating a compound of formula XIa in a known manner with an agent which yields the group $-COOR^8$, for example, a dialkyl or diphenyl carbonate or an alkyl or phenyl chloroformate, and reacting the resulting compound of formula XVa with a thiol of the formula $HS-CH_2-CHR^2-NHR^{33}$ in which $R^2$ is as previously described and $R^{33}$ is hydrogen or, where $R^{42}$ in the compound of formula XVa is hydrogen, also lower alkyl. This second step is preferably carried out at a temperature between about room temperature and the boiling point of the reaction mixture in an inert organic solvent, especially an ether such as diethyl ether, tetrahydrofuran and the like or a lower alcohol such as methanol and ethanol.

Alternatively, the compounds of formula XVa can be prepared by reacting a compound of formula VIII with a hydrazine of the formula $H_2N-NR^{42}-COOR^8$ in which $R^{42}$ and $R^8$ are as previously described. This reaction can be carried out in a known manner; for example, under the reaction conditions described above for process variant (b).

As mentioned above, it is not necessary, and in many cases also not possible, to isolate the compounds of formulas II, III, IV, V, VI and VIII. On the contrary, it has been found to be convenient as a rule to cyclize these compounds directly or to leave these compounds to cyclize without isolation from the reaction mixture in which they have been prepared.

The compounds of formula IX used as starting materials and the compounds of formulas II, III, IV, V, VI, VII and XI in which $R^5$ is lower alkyl, lower alkenyl, lower alkynyl or lower alkyl substituted by halogen or lower alkoxy can be prepared from compounds of formula XIII in accordance with Formula Scheme II hereinafter in which $R^1$, $R^2$, $R^{31}$, $R^{41}$, $R^{42}$, $R^{51}$, $R^6$, $R^7$, $R^8$, X and $X'$ are as previously described. The compounds of formula XIII belong to a known class of substances.

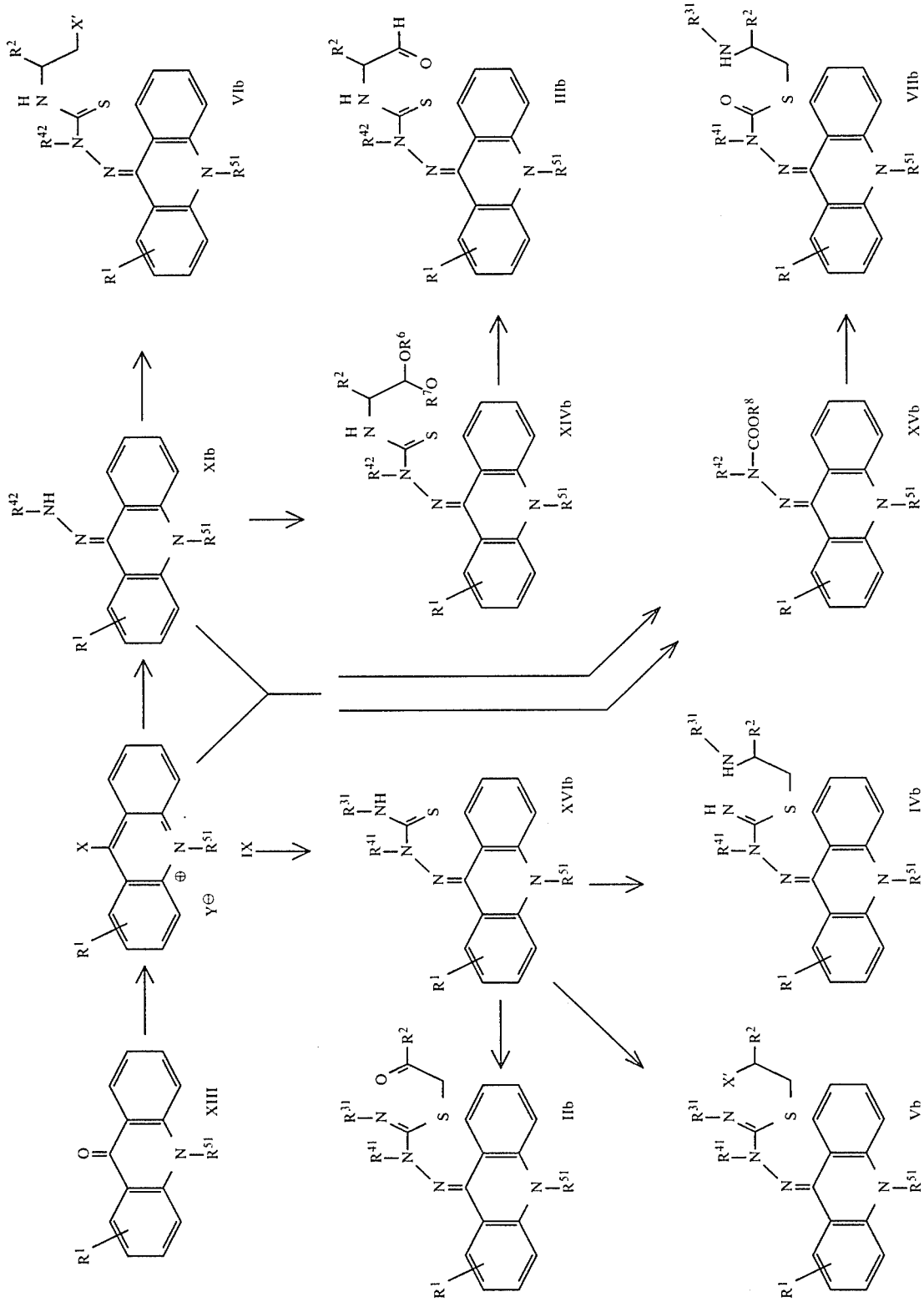

In Reaction Scheme II, those compounds of formula IX in which X is halogen can be prepared by treating a compound of formula XIII in an inert organic solvent wth a halogenating agent. In a preferred embodiment, oxalyl chloride or phosphorus oxychloride is used as the halogenating agent and a halogenated hydrocarbon such as methylene chloride, chloroform, 1,2-dichloroethane or the like, acetonitrile or excess halogenating agent is used as the solvent, there is obtained a compound of formula IX in which X is chlorine. The reaction temperatures advantageously vary in a range of about room temperature to the boiling point of the reaction mixture.

Compounds of formula IX in which X is a leaving group other than halogen can be obtained from the corresponding halogen compounds. For example, the halogen in such a compound can be replaced in a known manner by other leaving groups, for example, by lower alkoxy or lower alkanoyloxy.

The compounds of formula IX are quaternary ammonium salts, of which some, as mentioned earlier, are not particularly stable. Those compounds are conveniently processed immediately after their preparation. The nature of the anion denoted by $Y^{\ominus}$ depends on the manner in which the corresponding compound of formula IX has been prepared. For example, if a compound of formula IX in which X is chlorine is prepared and oxalyl chloride is used as the halogenating agent, then there is obtained a compound of formula IX in which $Y^{\ominus}$ is a chloride anion; if phosphorus oxychloride is used as the halogenating agent, then there is obtained a corresponding compound in which $Y^{\ominus}$ is $PO_2Cl_2^{\ominus}$.

The compounds of fomulas IIb, IIIb, IVb, Vb, VIb, VIIb and XIb can be prepared from compounds of formula IX in analogy to the preparation of the corresponding compounds which are substituted on the acridanone nitrogen atom by hydrogen from compounds of formula VIII. The compounds of formulas II, III, IV, V, VI and VII used as starting materials also form part of the invention.

The acridanone derivatives of formula I above and their pharmaceutically acceptable acid addition salts possess valuable pharmacological properties. In particular, the compounds of formula I possess valuable schistosomicidal activities and can accordingly be used in the control or prevention of schistosomiasis.

The schistosomicidal activity of the acridanone derivatives of formula I and their pharmaceutically acceptable acid addition salts can be demonstrated in an animal test as follows:

Albino mice weighing 15–18 g are infected subcutaneously with 60±5 cercaria of a Liberia strain of Schistosoma mansoni. Forty-six (46) days after infection, the animals are treated once perorally with the test substance. There are 5–10 animals used per substance and dosage. There are 10 untreated animals used as controls. The autopsies are carried out after 60 days. Whereupon worm pairs and individual worms in the mesenteric veins, portal vein and liver are dissected out and counted. The activity of the test substance shows itself in a reduced number of living parasites in comparsion to the number in the control animals.

For the evaluation, the percentage reduction in parasites in treated animals in comparison to untreated control animals is calculated. The $VD_{50}$ is determined according to the Probit method. The $VD_{50}$ is that vermicidal dosage which brings about a 50 percent reduction in the number of worms.

The Table which follows contains the results obtained with representative compounds of the invention. In the Table there are given $VD_{50}$ in mg/kg p.o. and the $LD_{50}$ in mg/kg in the case of single oral administration to mice.

TABLE

| Compound of formula I | $VD_{50}$ in mg/kg p.p. | $LD_{50}$ in mg/kg p.o. |
|---|---|---|
| 9-Acridanone (2-thiazolidinylidene)hydrazone | 26 | 1250–2500 |
| 10-Methyl-9-acridanone (2-thiazolyl)hydrazone hydrochloride | 9 | >5000 |

The acridanone derivatives of formula I and their pharmaceutically acceptable acid addition salts can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions.

For the preparation of pharmaceutical compositions, the acridanone derivatives of formula I and their pharmaceutically acceptable acid addition salts can be processed with pharmaceutically inert inorganic or organic carriers. Examples of carriers which can be used for tablets, coated tablets, dragees and hard gelatin capsules are lactose, maize starch or derviatives thereof, talc, stearic acid or its salts and the like. Suitable carriers for soft gelatin capsules are, for example, vegetable oils, waxes, fats, semi-solid and liquid polyols and the like. However, depending on the nature of the active substance, no carriers are generally required in the case of soft gelatin capsules. Suitable carriers for the preparation of solutions and syrups are, for example, water, polyols, saccharose, invert sugar, glucose and the like.

In addition, the pharmaceutical compositions can contain preserving agents, solubilizers, stabilizing agents, wetting agents, emulsifying agents, sweetening agents, coloring agents. flavoring agents, salts for varying the osmotic pressure, buffers, coating agents or antioxidants. They can also contain still other therapeutically valuable substances.

As mentioned earlier, medicaments containing an acridanone derivative of formula I or a pharmaceutically acceptable acid addition salt thereof are also an object of the invention, as is a process for the preparations of such medicaments, which process comprises bringing one or more acridanone derivatives of formula I or pharmaceutically acceptable acid addition salts thereof and, if desired, one or more other therapeutically valuable substances into a galenical administration form.

As mentioned earlier, the acridanone derivatives of formula I and their pharmaceutically acceptable acid addition salts can be used in the control or prevention of illnesses, and are especially suitable for the control or prevention of schistosomiasis. The dosage can vary within wide limits and is, of course, fitted to the individual requirements in each particular case. In general, a single oral administration of about 1 to about 50 mg/kg body weight should be appropriate for the treatment of schistosomiasis.

The Examples which follow further illustrate the invention. In the Examples, all temperatures are given in degrees Centigrade, unless otherwise stated.

EXAMPLE 2

(a) 1.0 g of 9-chloroacridine, 0.926 g of 2-hydrazino-2-thiazoline hydrobromide and 0.767 g of anhydrous sodium acetate are dissolved in 100 ml of dry ethanol, heated to boiling under reflux for 2 hours and the red solution is then evaporated in vacuo. The residue is treated with water and the crystalline mass is filtered under suction. After recrystallization from ethanol, there is obtained 9-acridanone (2-thiazolidinylidene)hydrazone of melting point 212°–216° (decomposition).

In an analogous manner there is obtained:

(b) From 9-chloroacridine and N-methyl-N-(2-thiazolin-2-yl)hydrazine hydrochloride the 9-acridanone methyl (2-thiazolin-2-yl)hydrazone of melting point 242°–243°.

EXAMPLE 2

2.09 g of 9-methoxyacridine are dissolved in 50 ml of dry ethanol, treated with a solution of 1.98 g of 2-hydrazino-2-thiazoline hydrobromide in 50 ml of dry ethanol, heated to boiling under reflux for 1 hour and the solvent is removed in vacuo. The residue is treated with aqueous ammonia (1:5) and extracted with ethyl acetate. After drying the extract over sodium sulfate and evaporation, the material obtained is crystallized by the addition of pentane. There is obtained 9-acridanone (2-thiazolidinylidene)hydrazone of melting point 214°–215° (decomposition).

EXAMPLE 3

A mixture of 2.3 g of 9-chloro-1-nitroacridine, 1.65 g of N-methyl-N-(2-thiazolyl)hydrazine hydrochloride and 100 ml of dimethylformamide is stirred at room temperature for about 18 hours. The dark red solution is evaporated, whereupon the residue is made alkaline with sodium carbonate solution and extracted with methylene chloride. The extract is washed with water, dried over sodium sulfate and evaporated. The residue is taken up in ethanol, acidified with ethanolic hydrochloric acid and the product is precipitated by the addition of ether. After filtration and washing with ether and petroleum ether, the hygroscopic salt is dried over phosphorus pentoxide. There is obtained 1-nitro-9-acridanone methyl (2-thiazolyl)hydrazone hydrochloride of melting point 185° (decomposition).

EXAMPLE 4

5.0 g of 9-chloro-1-nitroacridine, 3.8 g of 2-hydrazino-2-thiazoline hydrobromide and 3.17 g of anhydrous sodium acetate are dissolved in 250 ml of dry methanol, heated on a steam-bath for 1 hour and then left to stand overnight. The precipitated material is filtered and recrystallized from methanol. There is obtained 1-nitro-9-acridanone (2-thiazolidinylidene)hydrazone which beings to decompose from 152°.

EXAMPLE 5

3.12 g of 9-acridanone thiosemicarbazone and 2.33 g of 1-bromo-2-butylamine hydrobromide are heated to boiling under reflux in 100 ml of ethanol for 15 hours. The still hot solution is filtered and evaporated, whereupon the residue is made alkaline with sodium carbonate solution and extracted with methylene chloride. The extract is washed with water, dried over sodium sulfate and evaporated. After two-fold recrystallization from ethanol, there is obtained 9-acridanone [2-(4-ethyl)-thiazolidinylidene]hydrazone of melting point 101°–103°.

EXAMPLE 6

6.24 g of 9-acridanone thiosemicarbazone, 3.5 g of sodium acetate and 5.2 ml of chloroacetaldehyde (50 percent aqueous solution) in 200 ml of methanol are heated to boiling under reflux for 6 hours. After evaporation of the solvent, the residue is treated with water. The precipitated product is filtered and washed successively with water, a small amount of ethanol, ether and petroleum ether. There is obtained 9-acridanone (2-thiazolyl)hydrazone of melting point 208°–210° (decomposition).

EXAMPLE 7

(a) 3.3 g of 10-ethyl-9-acridanone are heated to boiling under reflux for 1.5 hours in 50 ml of phosphorus oxychloride, whereupon the solution is evaporated. The residue (10-ethyl-9-chloro-acridinium dichlorophosphate) is washed with ether, treated with 6.6 g of sodium acetate, 2.96 g of 2-hydrazino-2-thiazoline hydrobromide and 100 ml of methanol and the mixture is heated to boiling under reflux. After 1 hour, the crystallized-out material is filtered and washed successively with water, methanol and ether. There is obtained 10-ethyl-9-acridanone (2-thiazolidinylidene)hydrazone of melting point 187°–188°.

In an analogous manner there is obtained:

(b) From 10-methyl-9-acridanone and 2-hydrazino-2-thiazoline hydrobromide, the 10-methyl-9-acridanone (2-thiazolidinylidene)hydrazone of melting point 180°–181°;

(c) from 10-(n-butyl)-9-acridanone and 2-hydrazino-2-thiazoline hydrobromide, the 10-(n-butyl)-9-acridanone (2-thiazolidinylidene)hydrazone of melting point 170°–172°;

(d) from 10-allyl-9-acridanone and 2-hydrazino-2-thiazoline hydrobromide, the 10-allyl-9-acridanone (2-thiazolidinylidene)hydrazone of melting point 219°–221°;

(e) from 10-(2-methoxyethyl)-9-acridanone and 2-hydrazino-2-thiazoline hydrobromide, the 10-(2-methoxyethyl)-9-acridanone (2-thiazolidinylidene)hydrazone of melting point 188°–189°.

EXAMPLE 8

4.8 g of 1-nitro-9-acridanone are dissolved in 200 ml of dimethylformamide and treated with 0.5 g of sodium hydride. The deep red solution is treated with 2.5 ml of methyl iodide and stirred at room temperature for 4 hours. The yellow precipitate obtained is filtered and washed successively with dimethylformamide, water, ethanol and ether. There is obtained 10-methyl-1-nitro-9-acridanone of melting point 308°–309°.

4 g of 10-methyl-1-nitro-9-acridanone are heated to boiling under reflux in 100 ml of phosphorus oxychloride for 2 hours, whereupon the turbid solution is filtered and evaporated. The residue (1,9-dichloro-10-methyl-acridinium dichlorophosphate) is washed with ether, treated with 100 ml of methanol, 3.1 g of 2-hydrazino-2-thiazoline hydrobromide and 4 g of sodium acetate and heated to boiling under reflux. After 0.5 hour, the mixture is cooled and the red crystallizate is filtered. For purification, it is suspended in methanol, acidified with ethanolic hydrochloric acid and filtered. The filtrate is concentrated and made basic with diethylamine, whereupon the precipitated product is filtered and washed successively with ethanol, water and again with ethanol. After recrystallization from n-butanol, there is obtained 1-chloro-10-methyl-9-acridanone (2-thiazolidinylidene)hydrazone of melting point 206°–207°.

EXAMPLE 9

1.8 g of 10-methyl-9-acridanone are heated to boiling under reflux in 50 ml of phosphorus oxychloride for 1 hour, whereupon the solution is evaporated in vacuo. The residue is suspended in ether and filtered. The dried greenish powder, 9-chloro-10-methyl-acridinium dichlorophosphate, is dissolved in 100 ml of methanol, treated with 0.8 g of thiosemicarbazide and stirred at room temperature for 1 hour. The precipitated product is filtered, washed with ethanol and ether and heated to boiling for 10 minutes with 50 ml of concentrated ammonia. The mixture is filtered while hot and washed successively with water, ethanol and ether. There is obtained 10-methyl-9-acridanone thiosemicarbazone of melting point 196°–198° (decomposition).

1.9 g of 10-methyl-9acridanone thiosemicarbazone are suspended in 100 ml of methanol and stirred at 50° for 6 hours with 1.73 ml of chloroacetaldehyde (50percent aqueous solution). The mixture is concentrated, the crystalline product is filtered and washed successively with ethanol, water, ethanol and ether. There is obtained 10-methyl-9-acridanone (2-thiazolyl)hydrazone hydrochloride of melting point 224°–225° (decomposition).

EXAMPLE A

Preparation of tables of the following composition:

|  | mg/tablet |
|---|---|
| 10-Methyl-9-acridanone (2-thiazolyl)-hydrazone | 100 |
| Lactose | 100 |
| Maize starch | 85 |
| Povidone (Polyvinylpyrrolidone) | 10 |
| Talc | 3 |
| Magnesium stearate | 2 |
| Tablet weight | 300 |

The active substance is mixed with the lactose and the maize starch, moistened with an aqueous solution of Povidone and granulated. The granulate is dried at 40° and sieved. The sieved granulate is mixed with the talc and the magnesium stearate and the mixture is pressed into tablets.

We claim:

1. A compound of the formula

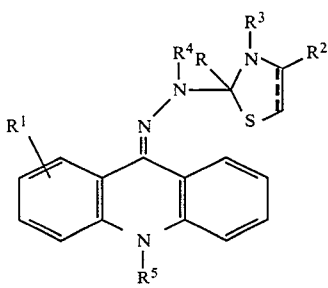

wherein the dotted line is an optional bond. R¹ is hydrogen, halogen or nitro, R² is hydrogen or lower alkyl, one of the substituents R³ and R⁴ is hydrogen or lower alkyl and the other together with R is an additional bond, and R⁵ is hydrogen, lower alkyl, lower alkenyl, lower alkynyl or lower alkyl substituted by halogen or lower alkoxy, or a pharmaceutically acceptable acid addition salt thereof.

2. A compound in accordance with claim 1, wherein R¹ is hydrogen.

3. A compound in accordance with claim 2, wherein R² is hydrogen.

4. A compound in accordance with claim 1, wherein R¹ is situated in the 1-position.

5. A compound in accordance with claim 4, wherein one of R³ and R⁴ is hydrogen and the other together with R is an additional bond.

6. A compound in accordance with claim 5, wherein R⁵ is hydrogen or lower alkyl.

7. A compound in accordance with claim 6, 10-methyl-9-acridanone (2-thiazolyl)hydrazone.

8. A compound selected from the group consisting of 9-acridanone (2-thiazolidinylidene)hydrazone, 9-acridanone (2-thiazolyl)hydrazone, 10-methyl-9-acridanone (2-thiazolidinylidene)hydrazone, 10-ethyl-9-acridanone (2-thiazolidinylidene)hydrazone, 9-acridanone methyl(2-thiazolinyl)hydrazone and 10-(2-methoxyethyl)-9-acridanone (2-thiazolidinylidene)hydrazone.

9. A schistosomicidal composition comprising an effective amount of a compound of the formula

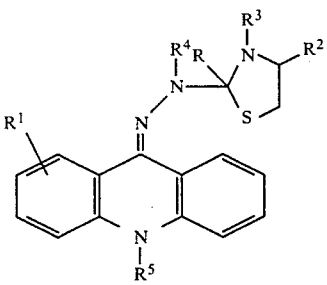

wherein the dotted line is an optional bond, R¹ is hydrogen, halogen or nitro, R² is hydrogen or lower alkyl, one of the substituents R³ and R⁴ is hydrogen or lower alkyl and the other together with R is an additional bond, and R⁵ is hydrogen, lower alkyl, lower alkenyl, lower alkynyl or lower alkyl substituted by halogen or lower alkoxy, or a pharmaceutically acceptable acid addition salt thereof, and a pharmaceutically inert carrier.

10. A schistosomicidal composition in accordance with claim 9, wherein the compound of formula I is 10-methyl-9-acridanone (2-thiazolyl)hydrazone.

11. A method of treating or preventing schistosomiasis which comprises administering to a mammalian host an effective amount of a compound of the formula

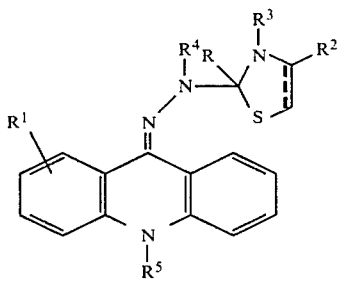

wherein the dotted line is an optional bond, $R^1$ is hydrogen, halogen or nitro, $R^2$ is hydrogen or lower alkyl, one of the substituents $R^3$ and $R^4$ is hydrogen or lower alkyl and the other together with R is an additional bond, and $R^5$ is hydrogen, lower alkyl, lower alkenyl, lower alkynyl or lower alkyl substituted by halogen or lower alkoxy, or a pharmaceutically acceptable acid addition salt thereof.

12. A method of treating schistosomiasis in accordance with claim 11, wherein the compound of formula I is 10methyl-9-acridanone (2-thiazolyl)hydrazone.

13. A compound of the formula

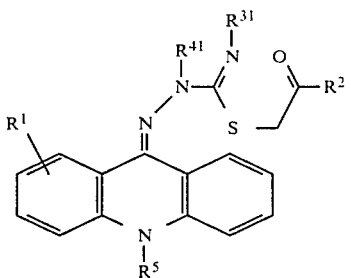

wherein $R^1$ is hydrogen, halogen or nitro, $R^2$ is hydrogen or lower alkyl, $R^5$ is hydrogen, lower alkyl, lower alkenyl, lower alkynyl or lower alkyl substituted by halogen or lower alkoxy, and one of $R^{31}$ and $R^{41}$ is hydrogen or lower alkyl and the other is hydrogen.

14. A compound of the formula

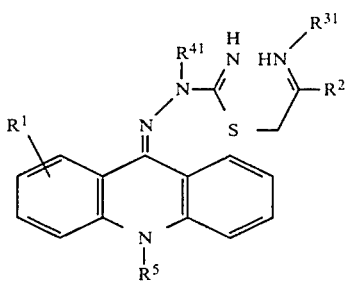

wherein $R^1$ is hydrogen, halogen or nitro, $R^2$ is hydrogen or lower alkyl, $R^5$ is hydrogen, lower alkyl, lower alkenyl, lower alkynyl or lower alkyl substituted by halogen or lower alkoxy, and one of $R^{31}$ and $R^{41}$ is hydrogen or lower alkyl and the other is hydrogen.

15. A compound of the formula

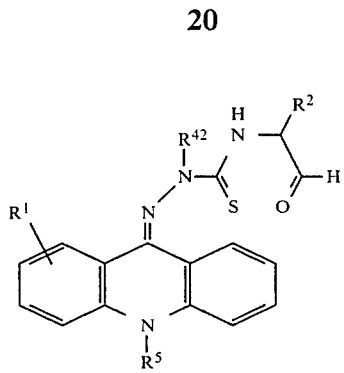

wherein $R^1$ is hydrogen, halogen or nitro, $R^2$ is hydrogen or lower alkyl, $R^5$ is hydrogen, lower alkyl, lower alkenyl, lower alkynyl or lower alkyl substituted by halogen or lower alkoxy, and $R^{42}$ is hydrogen or lower alkyl.

16. A compound of the formula

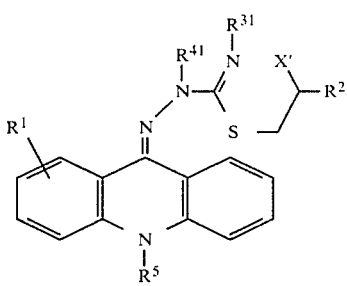

wherein $R^1$ is hydrogen, halogen or nitro, $R^2$ is hydrogen or lower alkyl, $R^5$ is hydrogen, lower alkyl, lower alkenyl, lower alkynyl or lower alkyl substituted by halogen or lower alkoxy, one of $R^{31}$ and $R^{41}$ is hydrogen or lower alkyl and the other is hydrogen, and X' is a halogen atom.

17. A compound of the formula

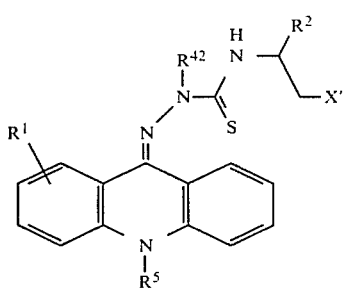

wherein $R^1$ is hydrogen, halogen or nitro, $R^2$ is hydrogen or lower alkyl, $R^5$ is hydrogen, lower alkyl, lower alkenyl, lower alkynyl or lower alkyl substituted by halogen or lower alkoxy, $R^{42}$ is hydrogen or lower alkyl, and X' is a halogen atom.

18. A compound of the formula

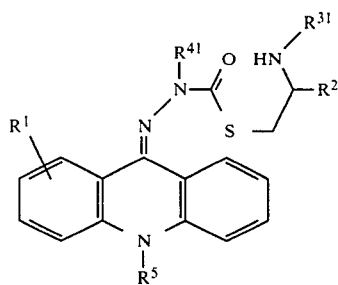
VII
wherein $R^1$ is hydrogen, halogen or nitro, $R^2$ is hydrogen or lower alkyl, $R^5$ is hydrogen, lower alkyl, lower alkenyl, lower alkynyl or lower alkyl substituted by halogen or lower alkoxy, and one of $R^{31}$ and $R^{41}$ is hydrogen or lower alkyl and the other is hydrogen.
* * * * *